US00PP34845P2

(12) United States Plant Patent
Spil

(10) Patent No.: US PP34,845 P2
(45) Date of Patent: Dec. 13, 2022

(54) ***HEUCHERA* PLANT NAMED 'IFHESBS'**

(50) Latin Name: *Heuchera hybrida*
Varietal Denomination: IFHESBS

(71) Applicant: INNOFLORA PLANT BREEDING B.V., Heerhugowaard (NL)

(72) Inventor: Glenn Spil, Zuidermeer (NL)

(73) Assignee: INNOFLORA PLANT BREEDING B.V., Heerhugowaard (NL)

( * ) Notice: Subject to any disclaimer, the term of this patent is extended or adjusted under 35 U.S.C. 154(b) by 0 days.

(21) Appl. No.: 17/838,851

(22) Filed: Jun. 13, 2022

(51) Int. Cl.
*A01H 5/02* (2018.01)
*A01H 6/80* (2018.01)

(52) U.S. Cl.
USPC ..... Plt./440

(58) Field of Classification Search
USPC ..... Plt./263.1, 440
See application file for complete search history.

*Primary Examiner* — Karen M Redden
(74) *Attorney, Agent, or Firm* — C. Anne Whealy

(57) ABSTRACT

A new and distinct cultivar of *Heuchera* plant named 'IFHESBS', characterized by its compact and uniformly mounded plant habit; moderately vigorous to vigorous growth habit and relatively rapid growth rate; densely foliated and bushy appearance; leaves that are initially yellow green in color with distinct venation becoming yellow with development; leaves that are relatively tolerant to high light conditions; numerous inflorescences with light pink-colored flowers; and good garden performance and winter hardiness.

2 Drawing Sheets

Figure 1:
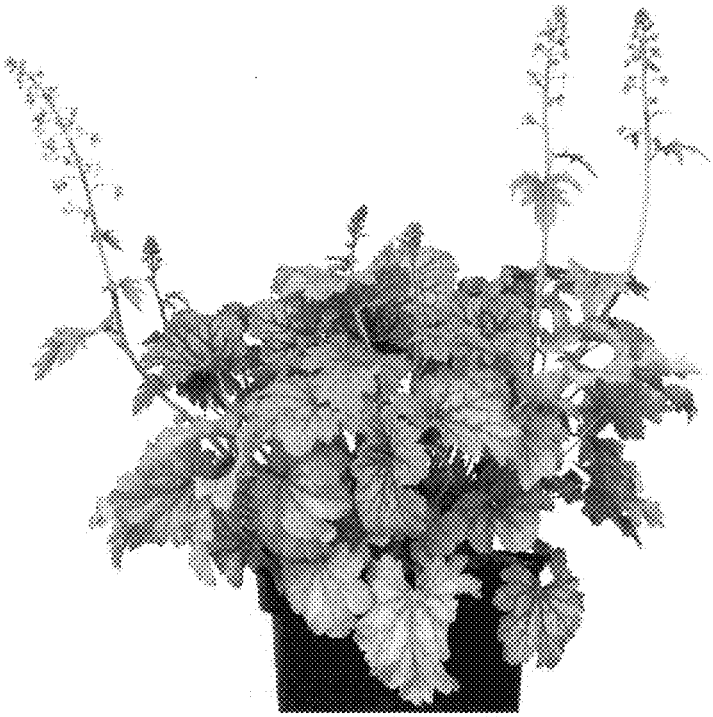

Botanical designation: *Heuchera hybrida.*
Cultivar denomination: 'IFHESBS'.

STATEMENT REGARDING PRIOR DISCLOSURES BY INVENTOR & APPLICANT/ASSIGNEE

An European Plant Breeder's Rights application for the instant plant was filed by the Applicant/Assignee, Innoflora Plant Breeding B.V. of Heerhugowaard, The Netherlands on Nov. 30, 2021, application number 2021/3090. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct *Heuchera* plant, botanically known as *Heuchera hybrida*, typically grown as a landscape *Heuchera* and hereinafter referred to by the name 'IFHESBS'.

The new *Heuchera* plant is a product of a planned breeding program conducted by the Inventor in Andijk, The Netherlands. The objective of the breeding program is to create new compact *Heuchera* plants with attractive leaf and flower coloration and good garden performance.

The new *Heuchera* plant originated from a cross-pollination of a proprietary selection of *Heuchera hybrida* identified as code number 083-13-K064-01, not patented, as the female, or seed, parent with a proprietary selection of *Heuchera hybrida* identified as code number 083-13-K037-03, not patented, as the male, or pollen, parent in April, 2015. The new *Heuchera* plant was discovered and selected as a single plant from within the progeny of the stated cross-pollination in a controlled environment in Heerhugowaard, The Netherlands in August, 2016.

Asexual reproduction of the new *Heuchera* plant by in vitro meristem culture in a controlled environment in Heerhugowaard, The Netherlands since September, 2016 has shown that the unique features of this new *Heuchera* plant are stable and reproduced true to type in successive generations.

SUMMARY OF THE INVENTION

The new *Heuchera* plant has not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'IFHESBS'. These characteristics in combination distinguish 'IFHESBS' as a new and distinct *Heuchera* plant:

1. Compact and uniformly mounded plant habit.
2. Moderately vigorous to vigorous growth habit and relatively rapid growth rate.
3. Densely foliated and bushy appearance.
4. Initially yellow green-colored leaves with distinct venation becoming yellow with development.
5. Leaves that are relatively tolerant to high light conditions.
6. Numerous inflorescences with light pink-colored flowers.
7. Good garden performance and winter hardiness.

Plants of the new *Heuchera* differ primarily from plants of the female parent selection in the following characteristics:

1. Leaf margins of plants of the new *Heuchera* are not as undulate as leaf margins of plants of the female parent selection.
2. Leaves of plants of the new *Heuchera* are more tolerant to high light conditions than leaves of plants of the female parent selection.

Plants of the new *Heuchera* differ primarily from plants of the male parent selection in the following characteristics:

1. Plants of the new *Heuchera* are more compact than plants of the male parent selection.
2. Leaves of plants of the new *Heuchera* are smaller than leaves of plants of the male parent selection.
3. Leaves of plants of the new *Heuchera* have more distinct venation than leaves of plants of the male parent selection.

Plants of the new *Heuchera* can be compared to plants of *Heuchera hybrida* 'Electra', disclosed in U.S. Plant Pat. No. 21,856. In side-by-side comparisons, plants of the new *Heuchera* differ primarily from plants of 'Electra' in the following characteristics:

1. Leaf margins of plants of the new *Heuchera* are more undulate than leaf margins of plants of 'Electra'.
2. Leaves of plants of the new *Heuchera* are initially yellow green in color becoming yellow with development whereas leaves of plants of 'Electra' have are lime green in color.

Plants of the new *Heuchera* can be compared to plants of *Heuchera hybrida* 'Red Lightning', disclosed in U.S. Plant Pat. No. 27,767. In side-by-side comparisons, plants of the new *Heuchera* differ primarily from plants of 'Red Lightning' in the following characteristics:

1. Leaf margins of plants of the new *Heuchera* are more undulate than leaf margins of plants of 'Red Lightning'.
2. Leaves of plants of the new *Heuchera* are more tolerant to high light conditions than leaves of plants of 'Red Lightning'.

BRIEF DESCRIPTION OF THE PHOTOGRAPHS

The accompanying colored photographs illustrates the overall appearance of the new *Heuchera* plant showing the colors as true as it is reasonably possible to obtain in colored reproductions of this type. Colors in the photographs may differ slightly from the color values cited in the detailed botanical description which accurately describe the colors of the new *Heuchera* plant.

The photograph on the first sheet (FIG. 1) is a side perspective view of a typical flowering plant of 'IFHESBS' grown in a container.

Figure 2:
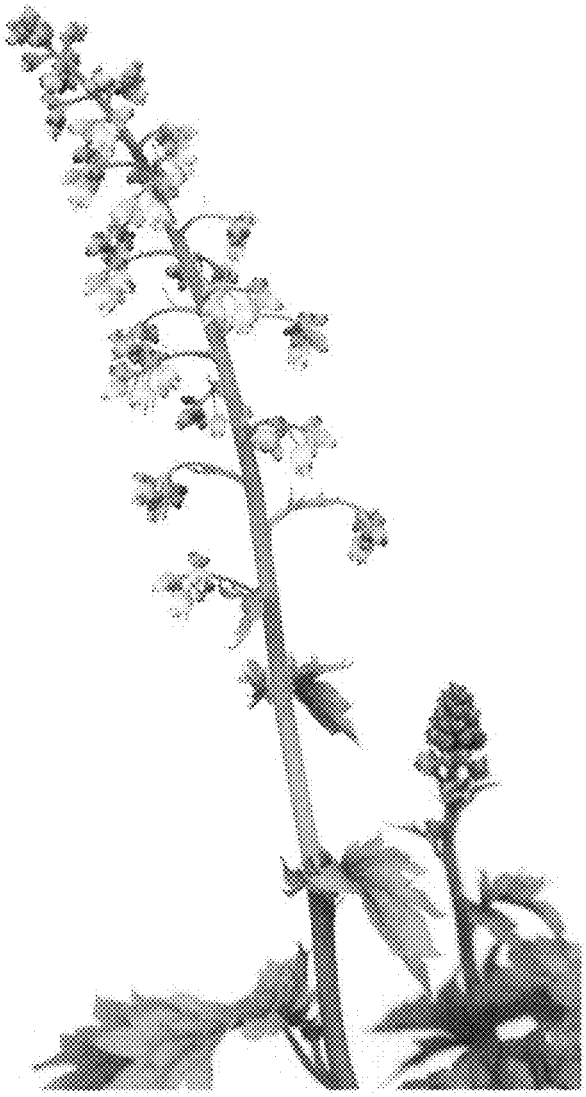

The photograph on the second sheet (FIG. 2) is a close-up view of a typical inflorescence of 'IFHESBS'.

DETAILED BOTANICAL DESCRIPTION

The aforementioned photographs and following observations, measurements and values describe plants grown during the spring in 3-liter containers in a greenhouse environment in Heerhugowaard, The Netherlands and under cultural practices typical of commercial *Heuchera* production. During the production of the plants, day temperatures ranged from 10° C. to 20° C. and night temperatures ranged from 10° C. to 13° C. Plants were 18 weeks old when the photographs and the description were taken. In the following description, color references are made to The Royal Horticultural Society Colour Chart, 2015 Edition, except where general terms of ordinary dictionary significance are used.

Botanical classification: *Heuchera hybrida* 'IFHESBS'.

Parentage:

*Female, or seed, parent*.—Proprietary selection of *Heuchera hybrida* identified as code number 083-13-K064-01, not patented.

*Male, or pollen, parent*.—Proprietary selection of *Heuchera hybrida* identified as code number 083-13-K037-03, not patented.

Propagation:

*Type*.—By in vitro meristem culture.

*Time to initiate roots, summer*.—About ten days at temperatures about 22° C.

*Time to initiate roots, winter*.—About 15 days at temperatures about 20° C.

*Time to produce a rooted young plant, summer*.—About 42 days at temperatures about 20° C.

*Time to produce a rooted young plant, winter*.—About 50 days at temperatures about 20° C.

*Root description*.—Fine, fibrous; typically light brown in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous perennial; basal rosette plant habit with leaves developing from the base; densely foliated and dense and bushy appearance; compact and uniformly mounded plant habit; overall shape, flattened globular with upright inflorescences held above the foliar plane; moderately vigorous to vigorous growth habit and relatively rapid growth rate.

*Plant height, soil level to top of foliar plane*.—About 23.6 cm.

*Plant height, soil level to top of inflorescences*.—About 40.6 cm.

*Plant diameter or spread*.—About 46 cm.

Leaf description:

*Arrangement*.—Alternate in basal rosettes; simple.

*Length*.—About 10.8 cm.

*Width*.—About 10.1 cm.

*Shape*.—Broadly ovate to close to orbicular; palmately lobed.

*Apex*.—Short and abruptly acute.

*Base*.—Hastate, lobes free to slightly imbricate.

*Margin*.—About seven to nine lobes per leaf; crenate with small abruptly acute tips; sinuses medium in depth and divergent; moderately undulate.

*Texture and luster, upper and lower surfaces*.—Moderately pubescent; not rugose; matte.

*Venation pattern*.—Palmate; reticulate.

*Color*.—Developing leaves, upper surface: Close to N144C; venation and area surrounding veins, close to 178B. Developing leaves, lower surface: Close to 145A; venation and area surrounding veins, close to 178B. Fully expanded leaves, upper surface: Close to 10A; towards the apex and margins, close to 7A; venation, close to 154B; area surrounding venation, close to 166B and 166C. Fully expanded leaves, lower surface: Close to 10A; towards the apex and margins, slightly tinged with close to 147D; venation, close to 145B to 145C; area surrounding venation, close to 199C and 199D.

*Petioles*.—Length: About 19.3 cm. Diameter: About 3 mm. Strength: Moderately strong. Texture and luster, upper and lower surfaces: Densely pubescent; slightly glossy. Color, upper surface: Close to 145A; proximally, close to 177C. Color, lower surface: Close to 145A; proximally, close to 152D

*Stipules*.—Quantity and arrangement: One at the base of each leaf. Length: About 1.5 cm. Width: About 2 mm. Shape: Roughly lanceolate with acute apex. Color, upper and lower surfaces: Close to 145B to 145C.

Flower description:

*Flower type and flowering habit*.—Single campanulate flowers arranged on axillary compound spikes; each spike with about 250 flowers; about 1,500 flowers develop per plant during the flowering season; flowers nodding to facing slightly outwardly.

*Fragrance*.—None detected.

*Time of flowering*.—Plants flower continuously from late spring into the summer in The Netherlands; plants begin flowering about 13 weeks after planting.

*Inflorescence longevity*.—Individual flowers last about a week on the plant; flowers not persistent.

*Inflorescence length*.—About 13.6 cm.

*Inflorescence width*.—About 4.6 cm.

*Flower diameter*.—About 7 mm.

*Flower depth* (*height*).—About 6 mm.

*Flower buds*.—Height: About 4 mm. Diameter: About 3 mm. Shape: Ovate. Texture and luster: Densely pubescent; matte. Color: Close to 150B; towards the base, close to 145A and towards the apex, close to 180A.

*Petals*.—Quantity and arrangement: Five petals in a single whorl. Length: About 4 mm. Width: About 0.8 mm. Shape: Oblanceolate. Apex: Acute. Base: Narrowly attenuate. Margin: Entire. Texture and luster, upper and lower surfaces: Smooth, glabrous; not rugose; matte. Color: When opening, upper and lower surfaces: Close to 69D. Fully opened, upper and lower surfaces: Close to 69D; venation, close to 69D; color does not change with subsequent development.

*Sepals*.—Quantity and arrangement: Five sepals in a single whorl; lower 60% fused. Length: About 5 mm. Width: About 1.2 mm. Shape: Free part, oblong. Apex: Obtuse. Margin: Entire. Texture and luster, upper surface: Smooth, glabrous; matte. Texture and luster, lower surface: Densely pubescent; matte. Color: When opening, upper surface: Close to 145C to 145D; towards the base, close to 145A to 145B and towards the apex, close to 180A. When opening, lower surface: Close to 154C; towards the base, close to 150B; distally, close to N144D and at the apex, close to 180A. Fully opened, upper surface: Close to 145C; towards the base, close to 13B; distally, close to 145A and towards the apex, close to 180A. Fully opened, lower surface: Close to 150B; distally, close to N144D and at the apex, close to 180A.

*Peduncles*.—Length: About 42.9 cm. Diameter: About 5 mm. Strength: Moderately strong. Aspect: About 30° to 70° from vertical. Texture and luster: Densely pubescent; moderately glossy. Color: Close to a blend of 144C and N144D.

*Pedicels*.—Length: About 3 mm. Diameter: About 0.8 mm. Strength: Moderately strong. Aspect: About 70° from peduncle axis. Texture and luster: Moderately pubescent; matte. Color: Close to 151A.

*Reproductive organs*.—Androecium: Stamen number: Five per flower. Filament length: About 3 mm. Filament color: Close to NN155B. Anther size: About 0.6 mm by 1 mm. Anther shape: Ovate. Anther color: Close to N200C to N200D. Amount of pollen: Scarce. Pollen color: Close to 155A. Gynoecium: Pistil number: Two per flower. Pistil length: About 3 mm. Style length: About 2.7 mm. Style color: Close to 150D. Stigma diameter: About 0.3 mm. Stigma shape: Club-shaped. Stigma color: Close to 157A. Ovary color: Close to 145B.

*Seeds and fruits*.—To date, seed and fruit development have not been observed on plants of the new *Heuchera*.

Pathogen & pest resistance: To date, plants of the new *Heuchera* have not been observed to be resistant to pathogens and pests common to *Heuchera* plants.

Garden performance: Plants of the new *Heuchera* have been observed to have good garden performance, to tolerate high light conditions and to tolerate temperatures from about −35° C. to about 35° C. and to be suitable for USDA Hardiness Zones 3 through 9.

It is claimed:

1. A new and distinct *Heuchera* plant named 'IFHESBS' as illustrated and described.

* * * * *